US006652751B1

United States Patent
Kutowy et al.

(10) Patent No.: US 6,652,751 B1
(45) Date of Patent: Nov. 25, 2003

(54) INTRINSICALLY BACTERIOSTATIC MEMBRANES AND SYSTEMS FOR WATER PURIFICATION

(75) Inventors: Oleh Kutowy, North Gower (CA); Carolyn Strlez, Gloucester (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/558,158

(22) Filed: Apr. 26, 2000

Related U.S. Application Data
(60) Provisional application No. 60/131,140, filed on Apr. 27, 1999.

(51) Int. Cl.[7] .............. B01D 71/06; B01D 39/00
(52) U.S. Cl. .............. 210/500.27; 210/502.1; 210/500.35; 210/500.41; 210/500.42; 264/41; 264/48; 264/49
(58) Field of Search .............. 210/500.27, 502.1, 210/500.35, 500.41, 500.42; 264/41, 48, 49

(56) References Cited

U.S. PATENT DOCUMENTS

| | | | | |
|---|---|---|---|---|
| 3,734,897 A | * | 5/1973 | Stoy | |
| 3,872,013 A | * | 3/1975 | Nishino et al. | |
| 3,953,545 A | * | 4/1976 | Stoy | |
| 4,032,688 A | * | 6/1977 | Pall | |
| 5,006,267 A | * | 4/1991 | Vaughn et al. | |
| 5,071,551 A | * | 12/1991 | Muramatsu et al. | |
| 5,102,547 A | * | 4/1992 | Waite et al. | |
| 5,180,585 A | * | 1/1993 | Jacobson et al. | |
| 5,433,987 A | * | 7/1995 | Peterson et al. | |
| 5,594,070 A | * | 1/1997 | Jacoby et al. | |
| 5,709,870 A | * | 1/1998 | Yoshimura et al. | |
| 5,762,797 A | * | 6/1998 | Patric et al. | |

FOREIGN PATENT DOCUMENTS

JP  2001-025773  *  1/2001

* cited by examiner

Primary Examiner—Ana Fortuna
(74) Attorney, Agent, or Firm—J. Wayne Anderson

(57) ABSTRACT

The invention disclosed relates to intrinsically bacteriostatic synthetic polymer membranes, and to process for the manufacture thereof. In one embodiment, bacteriostatic metal ions are attached to a surface of a preformed synthetic polymer membrane by static adsorption/adsorption and reduced to the metal in situ. In another embodiment, the intrinsically bacteriostatic membranes are formed by providing a casting solution of a membrane forming synthetic polymer and bacteriostatic metal ions, and casting into a bath containing a reducing agent for the metal ions to form the membrane containing the metal ions incorporated therein.

23 Claims, 6 Drawing Sheets

INTRINSICALLY BACTERIOSTATIC MEMBRANES AND SYSTEMS FOR WATER PURIFICATION

This application claims the benefit of Provisional application Ser. No. 60/131,140, filed Apr. 27, 1999.

BACKGROUND OF THE INVENTION

In potable water membrane purification systems, there are many surfaces that are normally contaminated by bacteria, causing rapid flux decline because of the bacteria themselves, or the slime they produce to attach themselves on surfaces.

It is well known that bacterostatic metal and metal ions can be used to address this problem. The metal and metal ions are chemically or non-chemically bonded to the membrane surface. The action of a bacteriostatic metal, which often includes toxic metals, needs to be on the active high pressure side of the membrane. It is mainly in this region that bacteria can colonize and cause pore blockage.

It is also known that it takes 2–30 ppb of dissolved silver to disinfect 20,000 gallons of water. However, a surface with a bacteriostatic metal e.g. silver and copper, will prevent microbial colonization. The mechanism is not known, but it is possible that even the lowest metal ion concentration (parts per billion) can be detected or "felt" by microorganisms and prevent their attachment and/or growth. It is believed by some that many forms of bacteria, fungus, and virus utilize a specific enzyme for their metabolism. Silver acts as a catalyst, effectively disabling the enzyme. It is toxic to all species tested of bacteria, protazoa, parasites, and many viruses, while copper is specific to fungi. To primitive life forms, silver is as toxic as the most powerful chemical disinfectants. However, this toxicity does not apply to higher life forms, which actually use some heavy metals in their metabolic pathways.

In U.S. Pat. No. 3,953,545, Stoy discloses the use of copper and silver ions as complexes with nitrile groups to be used in the formation of polymers and co-polymers. DuPont discloses in WO 94/15463 the use of barium particles successively coated with silver, copper oxide, silicon, hydrous alumina and droctyl azelate as powders for delustering fibers and providing anti-bacterial properties. A Japanese patent, JP 5,245,349, uses silver on zeolite particles that are added to a membrane formulation. There are many uses of various metals as antibacterial preparations in DuPont U.S. Pat. No. 5,180,585. Nitro, in JP 57084703 and Courtney, Gilehrist, and Park, in GB 1,521,171, disclose a silver "salt" or complex similar to U.S. Pat. No. 3,953,545.

Also, U.S. Pat. No. 5,102,547 discloses a synthetic polymer membrane incorporating fine particles of dispersed water-insoluble bioactive material e.g. metal and metal alloys linked to the polymer without chemical binding. Anti-bacterial activity is supposedly provided by the dissolving out of the metal. High metal concentrations of 0.05 to 15%/w, on a dry weight basis, are disclosed. It is noted that the application to water purification is not disclosed, and that in view of the disclosure of the use of several toxic metals antimony, bismuth and mercury, it is apparent that there is no contemplation of water treatment. It is also noted that the loose binding of the metals inside the porous matrix of the membrane instead of the active surface permits dissolution of the metals to the permeate without affecting the concentrate side of the membrane would result in the wastefull washing away of the metal in a water treatment system. This patent could be useful in supplying a source of metal ions to already treated water rather than preventing the fouling of treatment equipment (thus would not prevent fouling and flux decline of the membrane). The present invention, using a reductive technique, places only minute quantities (compared to the whole volume of the membrane) of porous metals such as silver copper and/or nickel at the very point of potential fouling by bacteria. It can also place metal or metal alloys, not only on the membrane surface, but on all surfaces in contact with the water that is being treated. In this way the system can be shut down having to add toxic bacteriostatic chemicals, and without the possibility of bacterial bloom.

To the best of the inventors' knowledge, there are presently no membranes or systems on the market that are intrinsically bacteriostatic, at the active separation surface layer.

SUMMARY OF THE INVENTION

It is an object of our invention to prevent the colorization of membrane surfaces by mircoorganisms when processing water.

The invention relates to a method and apparatus for rendering both systems and individual membranes toxic or otherwise incompatible to pathogens but harmless to animals, including humans. The invention provides a permanent solution to the deleterious effects of bacterial colonization and sliming of membrane systems. The membranes themselves separate all bacteria, viruses and cysts from drinking water in a cost-effective manner. In case adverse conditions affect or deteriorate the bacteriostatic properties of membranes and system, a simple reapplication of the treatment will be able to restore the bacteriostatic properties.

Due to their bacteriorstatic or other desirable properties, silver, copper, tin, nickel and other metals and/or mixtures and alloys are incorporated into a polymer membrane. Several methods can be employed to achieve the desired metal content: (1) adding a metal salt or mixture of compatible salts to the membrane polymer casting solution before formation of the film and gelling it into a bath containing sufficient reducing agent to deposit the metals; (2) once a membrane has been cast in the normal phase-inversion method, performing a static adsorption of soluble metal salts on the polymer membrane followed by exposure to a reducing agent, (3) incorporating the reducing agent into the membrane either as an additive before casting, (4) contacting the cast membrane with reducing agent and then contacting the membrane with the desired salt or mixture of compatible salts that deposit as metals, or (5) contacting the preformed membrane and/or water purification apparatus simultaneously with the metal salts and a reducing agent therefor.

Methods (2), (4) and (5) are preferred, since less metal is used. In Methods (1) and (3), the metal is incorporated in the matrix of the polymer. However, it takes considerably more metal incorporated into the polymer to have the same effect at the surface, as compared to the other methods.

The invention includes the choice of materials that are used and in the method of application.

DETAILED DESCRIPTION OF THE INVENTION

Figure 1:
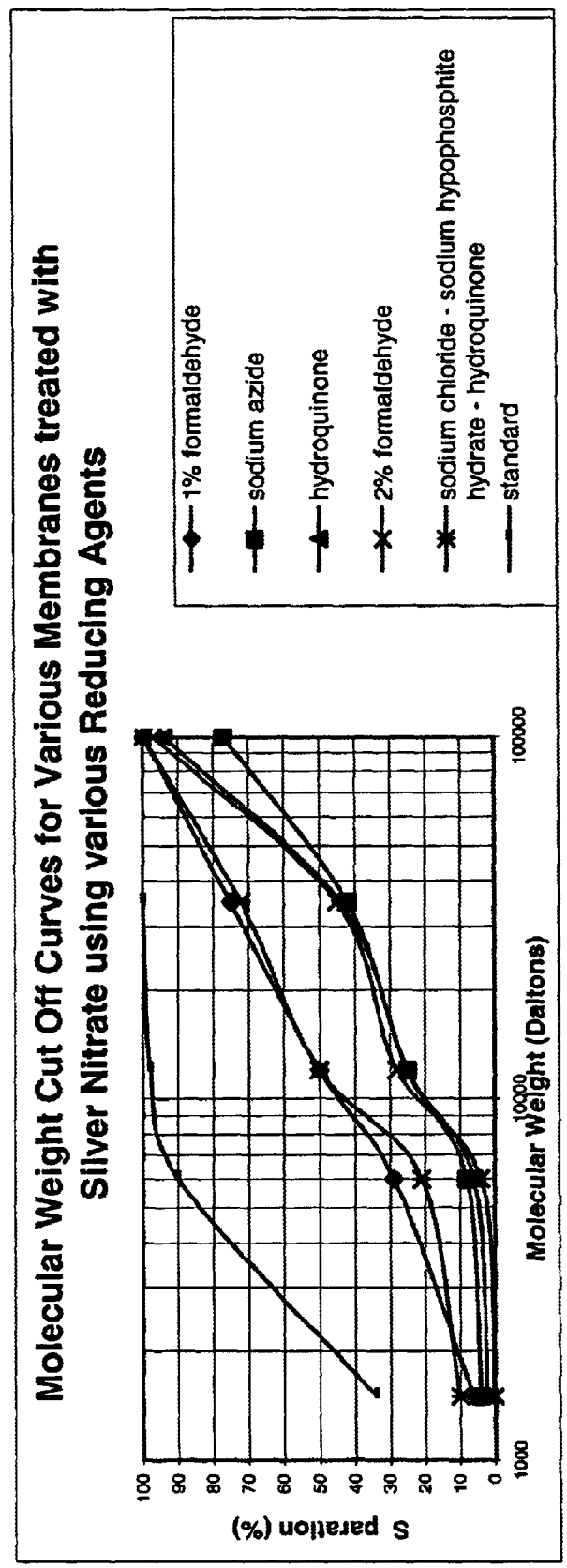
FIG. 1 is a graph, showing the effect of various reducing agents on membranes containing silver salts.

To achieve desired properties, metal or metal alloys are either incorporated into the membrane at the time of casting, as in the case of ultrafiltration and microfiltration membranes, and further enhanced by post treatment, or in the case of pre-formed membranes such as thin film composite reverse osmosis membranes or other preformed commercial membranes and systems, where the incorporation may not be possible or practical, the alloys are deposited and bound to all surfaces including the components of the module, pumps and plumbing. The procedures and methodology used for developing and evaluating the products in the inventions are described/summarized below:

Different Methods of Reducing Metals and Alloys in the Matrix of the Membrane

The inventors have identified a variety of suitable reducing agents for incorporating the metal into the membranes. For example: A membrane composed of 20% polyphenylsulfone, 20% polyvinylpyrrolidinone and 2% silver nitrate in 1-methyl-2-pyrrolidinone is cast onto polyester backing and gelled into 1% hydroquinone mixed with 1% formaldehyde. This membrane gives a flux rate of 446 Liters/square meters/hour (LMH) with a polyethylene glycol (PEG) separation of 78% at 35,000 Daltons (35K). The same polymer membrane gelled into 1% formaldehye gives a flux rate of 346 LMH and a PEG 35K separation of 75%.

The inventors have performed experiments with other reducing agents including sodium azide, potassium chloride, sodium iodide, sucrose, potassium sodium tartrate and mixtures and various concentrations of these (0.5 to 5% w/w). Although lower concentrations were effective, a standard value of 1% of reducing agent was used for most tests. Additionally, work with commercial plating solutions with a lower concentration was completed. Detailed examples of the method of reducing silver and/or copper and nickel into the matrix of the membrane by addition into the polymer solution are described.

Different Metals Fixated onto the Surface of the Membrane

Various concentrations of metals have been tested in the concentrations of 0.25 to 15% (w/w). For example: A membrane composed of 20% polyphenylsulfone and 20% polyvinylpyrrolidinone in 1-methyl-2-pyrrolidinone is cast onto polyester backing is gelled into water and a static adsorption is performed followed by a reduction. A static adsorption in 13% silver nitrate followed by 1% hydroquinonone produces a membrane that has a flux rate of 110 LMH and 87% separation of PEG 6K. A similar membrane after static adsorption in 6% silver nitrate followed by 1% hydroquinonone generates a membrane with a flux rate of 148 LMH and 93% separation of PEG 6K. Both of these membranes were negative for $E.$ $coli$ growth.

Work was completed on setting the limits of metal and reducer concentrations. Although lower concentrations were effective, a standard value of 6% metal salt and 1% reducing agent was used for most tests.

Tests were performed on various commercial and NRC-fabricated membranes of different materials and porosities. The change in pure water permeability rate after the treatment ranged from 0.422 for the polyvinylidene fluoride membrane, and 1.336 for the polyvinyl alcohol membrane. All membranes were viable after treatment. Tests performed with polyethersulfone-polyetherethersulfone co-polymer and polyphenylsulfone indicated that both polymers are suitable for silver treatment and therefore both were used for the majority of testing. According to visual methods, most of the other polymers tested had a metallic surface after static adsorption with 6% silver nitrate. These included both commercial and NRC membranes on a variety of backing materials.

Tests indicate certain conditions give better coating such as a very clean system (after a degreasing or caustic wash and pure water rinse) and higher temperature. Also, the system and membrane may be treated separately to obtain the best membrane porosity versus the requirements of the system coating. Components of the spiral wound module may be treated separately before winding (i.e. vexar and permeate carrier) to ensure an even coating. A membrane composed of 25% polyethersulfone-polyetherethersulfone co-polymer and 21% polyvinylpyrrolidinone in 1-methyl-2-pyrrolidinone is cast onto polyester backing and gelled into water and spiral wound into a module. The membrane was treated with 3% silver nitrate, drained and 1% hydroquinone was added. After treatment the module was dismantled and examined for coverage. Bacteria testing was negative for $E.$ $coli.$ Different Alloys Fixated onto the Surface of the Membranes The inventors have analyzed both a single reduction step and a multi-reduction step. In the first, the metals are introduced to the membrane and then the membrane is reduced in a second step. In a multi-reduction step, each metal salt is added separately and reduced before the next metal salt is introduced.

A membrane composed of 25% polyethersulfone-polyetherethersulfone co-polymer and 21% polyvinylpyrrolidinone in 1-methyl-2-pyrrolidinone is cast onto polyester backing, gelled into water and a single step static adsorption/reduction performed. Membranes treated in a 6% total 1:1:1 ratio of silver nitrate:cupric nitrate:tin sulfate, a 6% total 1:1:1 ratio of silver nitrate:nickelous nitrate:tin sulfate, and a 3% total 1:1:1 ratio of silver nickelous:nickel nitrate:cupric sulfate all tested negative for $E.$ $coli$ presence.

A membrane composed of 25% polyethersulfone-polyetherethersulfone co-polymer and 21% polyvinylpyrrolidinone in 1-methyl-2-pyrrolidinone is cast onto polyester backing is gelled into water and the multi-step method of reduction is used. A static adsorption in 6% silver nitrate and then reduction in 1% hydroquinonone followed by a static adsorption in 6% cupric nitrate and reduction in 1% hydroquinone is performed. This produces a membrane with a flux rate of 121 LMH and 96% separation of PEG 6K. The untreated membrane gives a flux rate of 167 LMH and 95% separation of PEG 6K giving a change in pure water permeability of 0.725.

The effects of relative ratios of incorporated metals in the range of 1 to 10% were evaluated. Although lower concentrations are effective, a standard value of 6% was chosen for the small scale.

Preferred Methods of Reducing Metals and Alloys in the Matrix of the Membrane

In this methods, the reducing agent is first introduced into the membrane, by incorporation as an additive before casting, as in the case of the use of hydroquinone, or by soaking of the formed or commercial membrane in a reducing agent solution chosen from hydroquinone, hydrazine, an aldehyde, sucrose, reducing salts as in a previous example. The reducing agent laden membrane is then sprayed, wiped or otherwise contacted with a metal salt or mixture of desired salts, to reduce them on the surface and in the porous matrix of any separation membrane. For example an 18% polyethersulfone-polyetherthersulfone co-polymer and 18% polyvinypyrrolidinone with 5% hydroquinone in 1-methyl-2-pyrrolidinone is cast onto polyolefin backing and gelled into 0.5% hydroquinone. A 6% silver nitrate solution is sponged on the surface of the membrane. The final membrane gives a pure water permeability of 659 LMH and 72% separation with PEG 35,000. An unmodified membrane gives a pure water flux rate of 512 LMH and 60% separation with PEG 35,000.

In all tests, at least three membranes of each type of treatment were tested for pure water permeability (PWP) and the molecular weight cut off determined by sieving methods with 200 ppm polyethylene glycols (PEG) and polyethylene oxide (PEO). Flux rates and separation data are determined at 345 kPa and 3.1 L/m, unless otherwise indicated. Percentage separations were determined by total carbon using a Shimadzu Total Organic Carbon Analyzer. In all examples given, the percentage of solutions used is based on weight/weight calculations.

The bacteria analysis was performed by Accu Test Laboratories Inc. in Nepean using standard *E. coli* determination and counting methods.

Metals in the Matrix of the Membrane

A 20% polyphenylsulfone (PPS), 20% polyvinylpyrrolidinone (PVP), and 2% silver nitrate in 1-methyl-2-pyrrolidinone solution is cast onto polyester backing and gelled into:

1% and 2% formaldehyde

1% sodium azide 0.5% and 1% hydroquinone

1% sodium chloride exposed to light and then into 1% sodium hypophosphite hydrate and then into 0.5% hydroquinone 1% sodium iodide and then 1% hydroquinone 1% hydrochloric acid and then 1% hydroquinone 1% silver nitrate and then 1% hydroquinone 1% hydroquinone mixed with 1% formaldehyde

TABLE 1

Observations of Membranes with Silver Nitrate Gelled in Reducing Agents

| Gellation | Membranes |
|---|---|
| 1% sodium chloride left in the light and then into 1% sodium hypophosphite hydrate and then to 0.5% hydroquinone | The membrane was a pinkish beige colour. |
| formaldehyde | The membrane was dark brown with lighter streaks. |
| Sodium azide | The membrane was dark brown with lighter streaks. |
| hydroquinone | The membrane was dark upon initial gellation and then turned an orangey-brown. A lighter surface could be wiped off. |
| Sodium iodide then hydroquinone | The membrane was a pinkish beige colour. |
| hydroquinone mixed with formaldehyde | The membrane was light beige with a darker surface that could be wiped off. |
| hydrochloric acid then hydroquinone | The membrane was orange and then turned a marbley brown/beige. |
| Silver nitrate then hydroquinone | The membrane immediately turned black and then slowly lightened. |
| Distilled water then hydroquinone | Nothing on surface of membrane. |
| hydroquinone mixed with formaldehyde | Membrane was grey in colour. |

TABLE 2

Flux and Separation Data of Membranes containing Silver Nitrate Gelled in Reducing Agents

| 20% PPS - 20% PVP 2% AgNO3 | PWP | 200 ppm PEG 35K | |
|---|---|---|---|
| Reduced into: | (LMH) | (LMH) | % sep |
| 1% formaldehyde | 346 | 247 | 75% |
| 1% sodium azide | 554 | 368 | 42% |
| 1% hydroquinone | 665 | 358 | 44% |
| 2% formaldehyde | 516 | 315 | 45% |
| 1% sodium chloride exposed to light then into 1% sodium hypophosphite hydrate and then 0.5% hydroquinone | 365 | 229 | 72% |
| 1% sodium iodide then 1% hydroquinone | 539 | 289 | 55% |
| 1% hydrochloric acid then 1% hydroquinone | 470 | 270 | 67% |
| 1% silver nitrate then 1% hydroquinone | 514 | 271 | 62% |
| 1% hydroquinone mixed with 1% formaldehyde | 446 | 259 | 78% |
| Standard | 292 | 205 | 99% |

A 20% polyphenylsulfone and 2% silver nitrate in 1-methyl-2-pyrrolidinone solution is cast onto polyester backing and gelled into 1% hydroquinone mixed with 1% formaldehyde. This was to determine the effects of polyvinylpyrrolidone (PVP) additive on metal deposition. The membrane with PVP gave a pure water flux rate of 446 LMH and flux rate with PEG 35K of 259 LMH (78% separation). The membrane with no PVP additive gave a pure water flux rate of 436 LMH and flux rate with PEG 35K of 307 LMH (70% separation).

FIG. 1 shows that the addition of metal salts to the polymer solution does change the original porosity of the membrane, but also that a feasible membrane is produced. To obtain a membrane with smaller pore sixes, an original membrane polymer solution producing smaller pores would be used for the addition of the metal salts.

A 18% polyethersulfone-polyetherethersulfone co-polymer (PES-PEES), 18% polyvinylpyrrolidinone (PVP), and 5% cupric choride in 1-methyl-2-pyrrolidinone solution is cast onto polyester backing and gelled into:

1. 0.5% formaldehyde 2. 0.5% formaldehyde then 6% silver nitrate 3. 0.5% hydroquinone 4. 0.5% hydroquinone then 6% silver nitrate 5. 0.5% silver nitrate

TABLE 3

Flux and Separation Data for Membranes containing Cupric Chloride in Reducing Agents

| 18% PES-PEES - 18% PVP - 5% CuCl$_2$ | PWP | 200 ppm PEG 6K | | 200 ppm PEG 35K | |
|---|---|---|---|---|---|
| Reduced into: | (LMH) | (LMH) | % sep | (LMH) | % sep |
| 0.5% formaldehyde | 751 | 666 | 7% | 369 | 44% |
| 0.5% formaldehyde then 6% silver nitrate | 582 | 525 | 22% | 355 | 76% |
| 0.5% hydroquinone | 210 | 208 | 73% | 185 | 97% |
| 0.5% hydroquinone then 6% silver nitrate | 255 | 251 | 70% | 214 | 99% |
| 0.5% silver nitrate | 499 | 470 | 26% | 311 | 68% |
| Standard | 512 | 378 | 48% | 345 | 60% |

The membrane gelled in formaldehyde produced a white membrane. The membrane gelled in hydroquinone had a pink/beige coloured membrane. When these membranes were put into silver nitrate, the membranes became a dark brown colour indicating the presence of silver. The membrane gelled in silver nitrate produced a brown coloured membrane, there were silver/grey particles in the solution indicating self reduction.

A 18% polyethersulfone-polyetherethersulfone co-polymer (PES-PEES), 18% polyvinylpyrrolidinone (PVP), and 5% nickelous nitrate in 1-methyl-2-pyrrolidinone solution is cast onto polyester backing and gelled into:
1. 0.5% hydroquinone
2. 0.5% hydroquinone then 6% silver nitrate
3. 0.5% hydroquinone then 6% cupric nitrate

TABLE 4

Flux and Separation Data for Membranes containing Nickelous Nitrate Gelled in Reducing Agents

| 18% PES-PEES - 18% PVP - 5% NiNO$_3$ | PWP | 200 ppm PEG 6K | | 200 ppm PEG 35K | |
|---|---|---|---|---|---|
| Reduced into: | (LMH) | (LMH) | % sep | (LMH) | % sep |
| 0.5% hydroquinone | 603 | 564 | 21% | 358 | 78% |
| Standard | 512 | 378 | 48% | 345 | 60% |

The nickel membrane was originally white. When it was put into a cupric nitrate solution, the membrane colour changed to a slightly beige/pink colour. Then the membrane was put into a 6% silver nitrate solution and the membrane immediately became dark brown. This indicated the original presence of nickel on the surface and pores of the membrane.

A 20% polyphenylsulfone, 20% polyvinylpyrrolidinone, and 2% silver nitrate in 1-methyl-2-pyrrolidinone solution is cast onto polyolefin backing and gelled into a bath of 156.6 g/L commercial developer solution (hydroquinone, p-methylaminophenol sulfate, sodium carbonate). This membrane gave pure water flux rates of 529 LMH and flux rates of 676 LMH (11% separation) with PEG 6K and 426 LMH (38% separation) with PEG 35K. This membrane has changed from a standard membrane which gives a pure after flux rate of 339 LMH and flux rate of 310 LMH (54% separation) with PEG 6K.

Metals Reduced on the Membrane with Static Adsorption

Method 1—Static Adsorption with One Metal Reduced with Hydroquinone

A membrane comprised of 25% polyphenylsulfone (PPS) and 21% polyvinylpyrrolidinone (PVP) in 1-methyl-2-pyrrolidinone solution cast onto polyester backing and gelled into reverse osmosis water is contacted with solutions of the following before reducing in 1% hydroquinone:

1%, 6%, 13% cupric sulfate
1%, 6%, 13% nickelous nitrate
6% nickel sulfate 1%, 6%, 13% silver nitrate
6% silver sulfate
1%, 6%, 13% tin sulfate
1%, 6%, 13% zinc nitrate
6% zinc sulfate

TABLE 5

Flux and Separation Data of Membranes with Adsorbed Metals

| 25% PPS - 21% PVP | Before Treatment | | | After Treatment | | | |
|---|---|---|---|---|---|---|---|
| all membranes reduced into 1% hydroquinone | PWP | 200 ppm PEG 6K | | PWP | 200 ppm PEG 6K | | change in |
| Adsorption of: | (LMH) | (LMH) | % sep | (LMH) | (LMH) | % sep | PWP |
| 1% cupric sulfate | 67 | 36 | 87% | 70 | 72 | 88% | 1.043 |
| 6% cupric sulfate | 101 | 77 | 89% | 111 | 109 | 90% | 1.099 |
| 13% cupric sulfate | 120 | | | 105 | 109 | 89% | 0.872 |
| 1% nickelous nitrate | 90 | 63 | 86% | 82 | 95 | 90% | 0.912 |
| 6% nickelous nitrate | 94 | 64 | 74% | 162 | 154 | 83% | 1.723 |
| 13% nickelous nitrate | 77 | 52 | 85% | 70 | 80 | 87% | 0.905 |
| 6% nickel sulfate | | | | 199 | 189 | 88% | |
| 1% silver nitrate | | | | 117 | 102 | 93% | |
| 3% silver nitrate | 147 | 228 | 78% | 112 | 139 | 94% | 0.762 |
| 6% silver nitrate | 206 | 219 | 89% | 148 | 163 | 93% | 0.718 |
| 13% silver nitrate | | | | 110 | 107 | 87% | |
| 6% silver sulfate | | | | 190 | 171 | 90% | |
| 1% tin sulfate | 128 | 77 | 89% | 94 | 97 | 95% | 0.735 |
| 6% tin sulfate | 109 | 83 | 80% | 133 | 121 | 78% | 1.220 |
| 13% tin sulfate | 112 | | | 82 | 86 | 95% | 0.736 |
| 1% zinc nitrate | 98 | 96 | 87% | 91 | 103 | 90% | 0.927 |
| 6% zinc nitrate | 87 | 63 | 89% | 154 | 152 | 90% | 1.770 |
| 13% zinc nitrate | 46 | 37 | 82% | 48 | 54 | 91% | 1.039 |
| 6% zinc sulfate | | | | 215 | 196 | 93% | |
| Standard (no metal salt additive, no treatment) | 202 | 219 | 64% | 181 | 185 | 91% | 0.896 |

Figure 2:
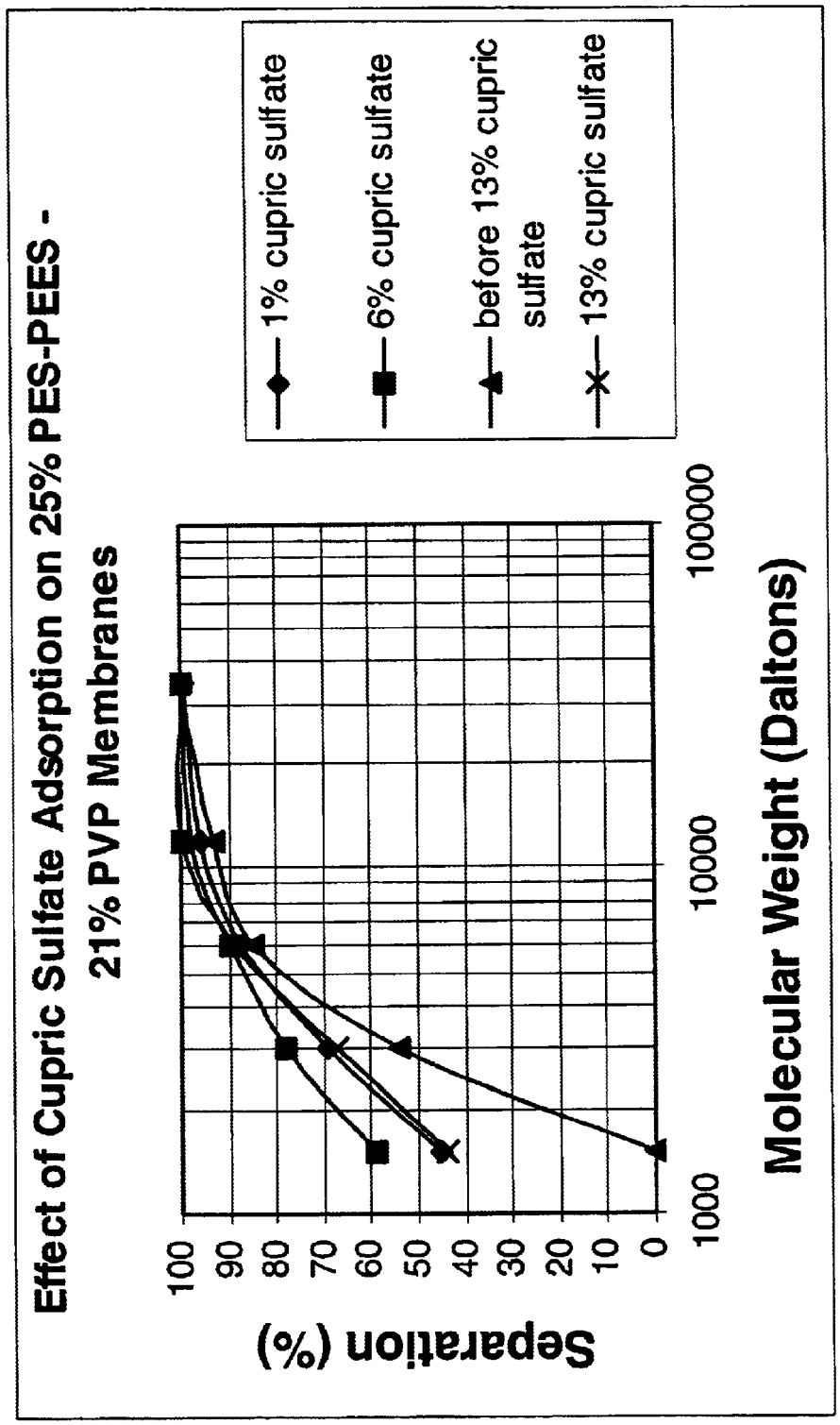
FIG. 2 is a graph illustrating the effect of the adsorption of various concentrations of copper metal into the membrane.

FIG. 2 shows that the adsorption of metals on the surface of the membrane does not drastically change the porosity of the membranes. Similar curves were obtained for the other metals.

Membranes were black after silver reduction. A whitish film could be wiped off but darker colour remained. The silver treated membranes were sent for bacteria testing and the control was positive for E. coli growth but all others were negative. There was a slight change in the cupric sulfate treated membranes, and the membrane became darker a few days later. All the others showed no initial change. One percent sodium hypophosphite was added to tin sulfate, zinc sulfate, nickel sulfate, zinc nitrate and nickelous nitrate. Still no change but a few days later there was more colour on the nickel membranes and a white precipitate in the tin sulfate solution.

Higher percentages of metal gave darker surface coatings. Higher amounts of hydroquinone accelerated the reaction. The tests were performed with 1% hydroquinone as a standard.

Other polymers were examined for silver adsorption with 6% silver nitrate then reduced into 1% hydroquinone. Polymers tried were polyethersulfone-polyetherethersulfone co-polymer, polyphenylsulfone, polyacrylonitrile, polyvinylidenefluoride, polyether-imide, cellulose acetate, polyamide-imide, acrylic, polysulfone, modified polysulfone, regenerated cellulose, thin-film composite, cellulose triacetate, and polyamide. A range of molecular weight cut offs were treated with 6% silver nitrate and then 1% hydroquinone. All membranes showed colour change which remained after testing.

Two spiral wound modules (4"×20") made with membrane of 25% polyethersulfone-polyetherethersulfone co-polymer and 21% polyvinylpyrrolidinone in 1-methyl-2-pyrrolidinone cast onto polyester backing gelled into reverse osmosis water were treated with 3% silver nitrate. To one spiral 1% hydroquinone was added directly. The other spiral was drained and then 1% hydroquinone was added. After testing, the spirals were dismantled to determine adsorption patterns. Most areas of the membrane were coated except for the areas directly underneath, in contact with and shielded by the spacer material. The spiral that was drained prior to reducing did not have reduced particulate matter in solution and caught in areas of the spiral as the spiral that hydroquinone was added directly to the silver nitrate solution. A piece of this membrane was tested for bacteria analysis and came back negative for E. coli growth. The flux rate through the membrane was 107 LMH at 345 kPa and 58 Liters/minute flow. The percentage separation of PEG 6K was 91% and PEG 35K was 99%. After initial cleaning with normal amounts of pure water flushed through the permeate lines, the permeate was negligible in desolved silver content.

Method 2—Static Adsorption with One Metal Reduced with Other Agents

A 25% polyphenylsulfone and 21% polyvinylpyrrolidinone in 1-methyl-2-pyrrolidinone solution cast onto polyester backing and gelled into reverse osmosis water was treated with solutions of 1% silver nitrate and 1.5% potassium sodium tartrate. This was acidified to pH 3.5 with hydrochloric acid. Once the membranes were added, ammonium hydroxide was added until the silver was reduced. All membranes were orange/brown after the dip. Whitish silver film could be wiped off with some difficulty but darker colour remained. After testing, the colour remained on the surface of the membranes. These membranes gave flux rates of 147 LMH of pure water and 144 LMH with 200 ppm PEG 6K (85% separation) before the treatment and gave flux rates of 131 LMH of pure water and 139 LMH with 200 ppm PEG 6K (84% separation) after the treatment. This demonstrates minimal changes in performance.

A 25% polyphenylsulfone (PPS) and 21% polyvinylpyrrolidinone (PVP) in 1-methyl-2-pyrrolidinone solution cast onto polyester backing and gelled into reverse osmosis water. These membranes were subjected to the following process: To 38 mL of a 7% silver nitrate solution, ammonium hydroxide was added drop by drop until the dark brown precipitate dissolved. 13 mL of 14% potassium hydroxide was added and ammonium hydroxide added drop by drop until the solution became clear. 15 mL of a solution of 6.5% dextrose in 17.5% of ethyl alcohol in distilled water was added. The solution was mixed for 1 minute and the membranes added. One series was completed at the previous concentrations, and the second was completed at 50% dilution of the amount of silver. Membranes were left in for 10, 15, 20, and 30 seconds, 5, 10 and 15 minutes. One membrane was contacted with the solutions with no ammonium hydroxide addition.

TABLE 6

Flux and Separation Data for Pore Size Ranges for Three Polymers Treated with Silver Nitrate

| 6% silver nitrate then 1% hydroquinone | Before Treatment | | | After Treatment | | | change in PWP |
|---|---|---|---|---|---|---|---|
| | PWP (LMH) | 200 ppm PEG 6K (LMH) | % sep | PWP (LMH) | 200 ppm PEG 6K (LMH) | % sep | |
| polysulfone 1,000 | 4 | 5 | 94% | 8 | 7 | 93% | |
| polysulfone 5,000 | 49 | 52 | 56% | 64 | 60 | 64% | 1.309 |
| polysulfone 10,000 | 856 | 845 | 8% | 867 | 915 | 5% | 1.013 |
| polysulfone 50,000 | 1372 | 1298 | 9% | 1400 | 1410 | 13% | 1.021 |
| polysulfone 100,000 | 1883 | 1952 | 6% | 2029 | 1996 | 7% | 1.077 |
| regenerated cellulose 2,000 | 402 | 441 | 9% | 438 | 574 | 9% | 1.089 |
| regenerated cellulose 5,000 | 72 | 70 | 95% | 74 | 76 | 92% | 1.022 |
| regenerated cellulose 10,000 | 99 | 104 | 99% | 110 | 102 | 100% | 1.104 |
| cellulose acetate 2,000 | 52 | 54 | 54% | 24 | 29 | 92% | 0.466 |
| cellulose acetate 20,000 | 153 | 106 | 28% | 84 | 140 | 27% | 0.548 |
| cellulose acetate 50,000 | 1666 | | | 1503 | 1631 | 0% | 0.902 |

TABLE 7

Flux and Separation Data for Membranes with Adsorbed Silver Nitrate Reduced with Dextrose

| 25% PPS - 21% PVP Reduced into 6.5% dextrose | Before Treatment | | | After Treatment | | | change |
|---|---|---|---|---|---|---|---|
| | PWP | 200 ppm PEG 6K | | PWP | 200 ppm PEG 6K | | |
| Adsorption of: | (LMH) | (LMH) | % sep | (LMH) | (LMH) | % sep | in PWP |
| 3.5% silver nitrate with 14% potassium hydroxide and ammonium hydroxide | 138 | 134 | 87% | 113 | 107 | 89% | 0.774 |
| 7% silver nitrate with 14% potassium hydroxide and ammonium hydroxide | 141 | 135 | 84% | 62 | 69 | 93% | 0.491 |
| 7% silver nitrate with 14% potassium hydroxide | 163 | 156 | 85% | 154 | 144 | 90% | 0.886 |
| Standard (no treatment) | 148 | 143 | 86% | 142 | 140 | 91% | 0.948 |

All membranes were orange/brown after the dip. A whitish silver film could be wiped off but the darker colour remained. After testing, the colour remained on the surface of most of the membranes.

Figure 3:
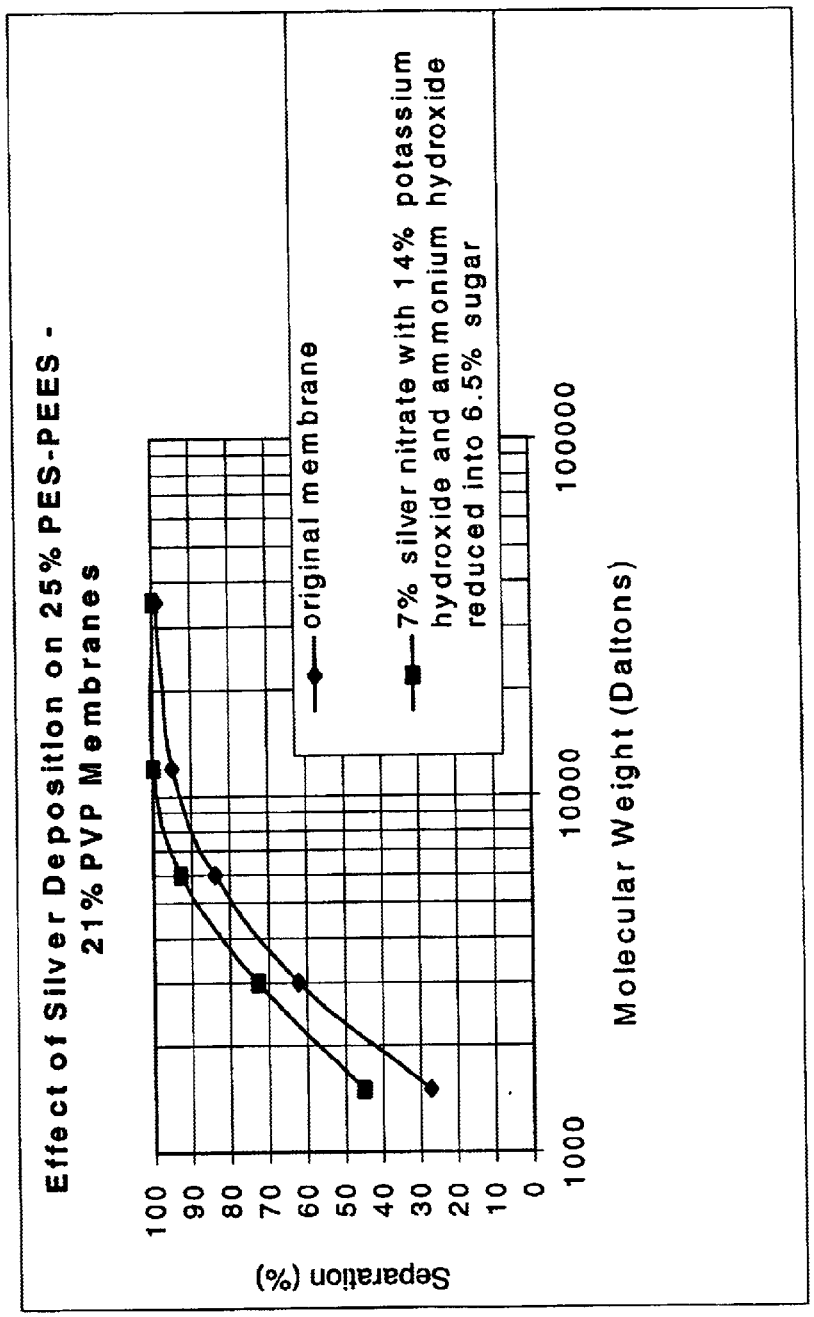
FIG. 3 is a graph illustrating the effect of absorption of silver metal on the membrane.

FIG. 3 shows the similarities in porosity of the membranes before and after treatment with the silver nitrate. This indicates that although silver has been deposited in the active surface area, the membrane retained its separation ability.

Various commercial and NRC membranes were subjected to the following process: To 38 mL of a 7% silver nitrate solution, ammonium hydroxide was added drop by drop until the dark brown precipitate dissolved. 13 mL of 14% potassium hydroxide was added and ammonium hydroxide added drop by drop until the solution became clear. 15 mL of a solution of 6.5% dextrose in 17.5% ethyl alcohol in distilled water was added. The solution was mixed for 1 minute and the membranes added and allowed to absorb for 5 minutes.

A 25% polyphenylsulfone and 21% polyvinylpyrrolidinone in 1-methyl-2-pyrrolidinone solution is cast polyester backing and gelled into reverse osmosis water. These membranes were subjected to a process using a 2.5% silver nitrate solution treated with ammonium hydroxide, then a 4.5% potassium hydroxide solution was added and both were treated with ammonium hydroxide. This was reduced with a 8% sugar in 1% alcohol with 0.5% nitric acid solution. Membranes were left in the solution for 5 minutes. All membranes were orange/brown after the dip. A whitish film could be wiped off but the darker colour remained. After testing, the colour remained on the surface of most of the membranes. These membranes gave flux rates of 135 LMH of pure water and 131 LMH with 200 ppm PEG 6K (87% separation) before the treatment and gave flux rates of 110 LMH of pure water and 105 LMH with 200 ppm PEG 6K (92% separation) after the treatment. This again demonstrates minimal performance changes.

Another process is performed using a heated 6% hydrazine sulfate to which a saturated cupric hydroxide is added

TABLE 8

Flux and Separation Data for Various Membrane Polymer Types with Adsorbed Silver Nitrate

| 3.5% silver nitrate with 14% potassium hydroxide and ammonium hydroxide reduced in 6.5% dextrose | Before Treatment | | | After Treatment | | | % change of PWP |
|---|---|---|---|---|---|---|---|
| | PWP | 200 ppm PEG 6K | | PWP | 200 ppm PEG 6K | | |
| | (LMH) | (LMH) | % sep | (LMH) | (LMH) | % sep | |
| modified polysulfone | 55 | 52 | 89% | 54 | 50 | 81% | 0.969 |
| polyacrylonitrile | 113 | 126 | 10% | 98 | 100 | 34% | 0.862 |
| polyamide-imide | 349 | 365 | 31% | 409 | 455 | 0% | 1.174 |
| polyetherethersulfone | 853 | 891 | 6% | 860 | 887 | 2% | 1.009 |
| polyether-imide | 32 | 54 | 93% | 42 | 40 | 95% | 1.327 |
| polyethersulfone | 179 | 167 | 94% | 44 | 39 | 51% | 0.248 |
| polyphenylsulfone | 91 | 45 | 82% | 99 | 98 | 82% | 1.089 |
| polysulfone | 23 | 24 | 92% | 27 | 27 | 94% | 1.171 |
| polyvinyl alcohol | 43 | 39 | 8% | 58 | 54 | 15% | 1.336 |
| polyvinylidene fluoride | 85 | 85 | 19% | 36 | 37 | 57% | 0.422 |
| thin film composite | 438 | 463 | 34% | 402 | 392 | 60% | 0.917 |

All membranes were orange/brown after the dip. The polyethersulfone, polyvinylidene fluoride and thin film composite membranes had a shiny surface. After testing, the colour remained on the surface of all of the membranes.

and ammonium hydroxide. The membranes were subjected to this solution. A solution of 1% potassium hydroxide is heated and added to the first solution containing the membranes. These membranes gave flux rates of 120 LMH of pure water and 116 LMH with 200 ppm PEG 6K (82% separation) before the treatment and gave flux rates of 124 LMH of pure water and 111 LMH with 200 ppm PEG 6K (90% separation) after the treatment. This shows minimal membrane porosity changes.

Alloys Reduced on the Membrane with Static Adsorption Method 1—Alloys Reduced in the Single Step Method with Hydroquinone A 25% polyethersulfone-polyetherethersulfone co-polymer and 21% polyvinylpyrrolidinone in 1-methyl-2-pyrrolidinone on polyester backing membranes cast into reverse osmosis water and subjected to the following solutions before reduction with 1% hydroquinone.

| 1.  | 6% total | 1:1:1 | silver nitrate:cupric nitrate:tin sulfate |
| 2.  | 6% total | 1:1:1 | silver nitrate:nickelous nitrate:tin sulfate |
| 3.  | 6% total | 1:1:1 | silver nitrate:nickelous nitrate:cupric nitrate |
| 4.  | 6% total | 1:1:1 | cupric nitrate:nickelous nitrate:tin sulfate |
| 5.  | 3% total | 1:1:1 | silver nitrate:cupric sulfate:tin sulfate |
| 6.  | 3% total | 1:1:1 | silver nitrate:nickelous nitrate:tin sulfate |
| 7.  | 3% total | 1:1:1 | silver nitrate:nickelous nitrate:cupric sulfate |
| 8.  | 3% total | 1:2   | silver nitrate:nickelous nitrate |
| 9.  | 3% total | 1:2   | silver nitrate:cupric sulfate |
| 10. | 3% total | 1:2   | silver nitrate:tin sulfate |
| 11. | 1% total | 1:1:1 | silver nitrate:nickelous nitrate:tin sulfate |

The membranes contacted with silver nitrate cupric nitrate:tin sulfate and silver nitrate:nickelous nitrate:tin sulfate were very dark. There was a coppery colour on the surface. The membranes treated with cupric nitrate:nickelous nitrate:tin sulfate solution showed only slight changes in surface colour.

TABLE 9

Flux and Separation Data for Membranes with Alloys Reduced by the Single Step Method

| 25% PES-PEES 21% PVP Gelled into 1% hydroquinone | PWP (LMH) | 200 ppm PEG 6K (LMH) | % sep | 200 ppm PEG 35K (LMH) | % sep |
|---|---|---|---|---|---|
| 1% total 1:1:1 silver nitrate:nickelous nitrate: tin sulfate | 226 | 232 | 65% | 243 | 100% |

TABLE 9-continued

Flux and Separation Data for Membranes with Alloys Reduced by the Single Step Method

| 25% PES-PEES 21% PVP Gelled into 1% hydroquinone | PWP (LMH) | 200 ppm PEG 6K (LMH) | % sep | 200 ppm PEG 35K (LMH) | % sep |
|---|---|---|---|---|---|
| 3% total 1:2 silver nitrate:nickelous nitrate | 217 | 221 | 79% | 226 | 100% |
| 3% total 1:2 silver nitrate:cupric sulfate | 208 | 207 | 72% | 219 | 100% |
| 3% total 1:1:1 silver nitrate:nickelous nitrate: tin sulfate | 225 | 227 | 70% | 231 | 100% |
| 6% total 1:1:1 cupric nitrate:nickelous nitrate: tin sulfate | 156 | 149 | 84% | 156 | 100% |
| 6% total 1:1:1 silver nitrate:nickelous nitrate: cupric nitrate | 118 | 105 | 92% | | |

The 6% total 1:1:1 silver nitrate:cupric sulfate:tin sulfate membrane, the 6% total 1:1:1 silver nitrate:nickelous nitrate:tin sulfate membrane, and the 3% total 1:1:1 silver nitrate:nickelous nitrate:cupric sulfate were negative for *E. coli* testing.

Figure 4:
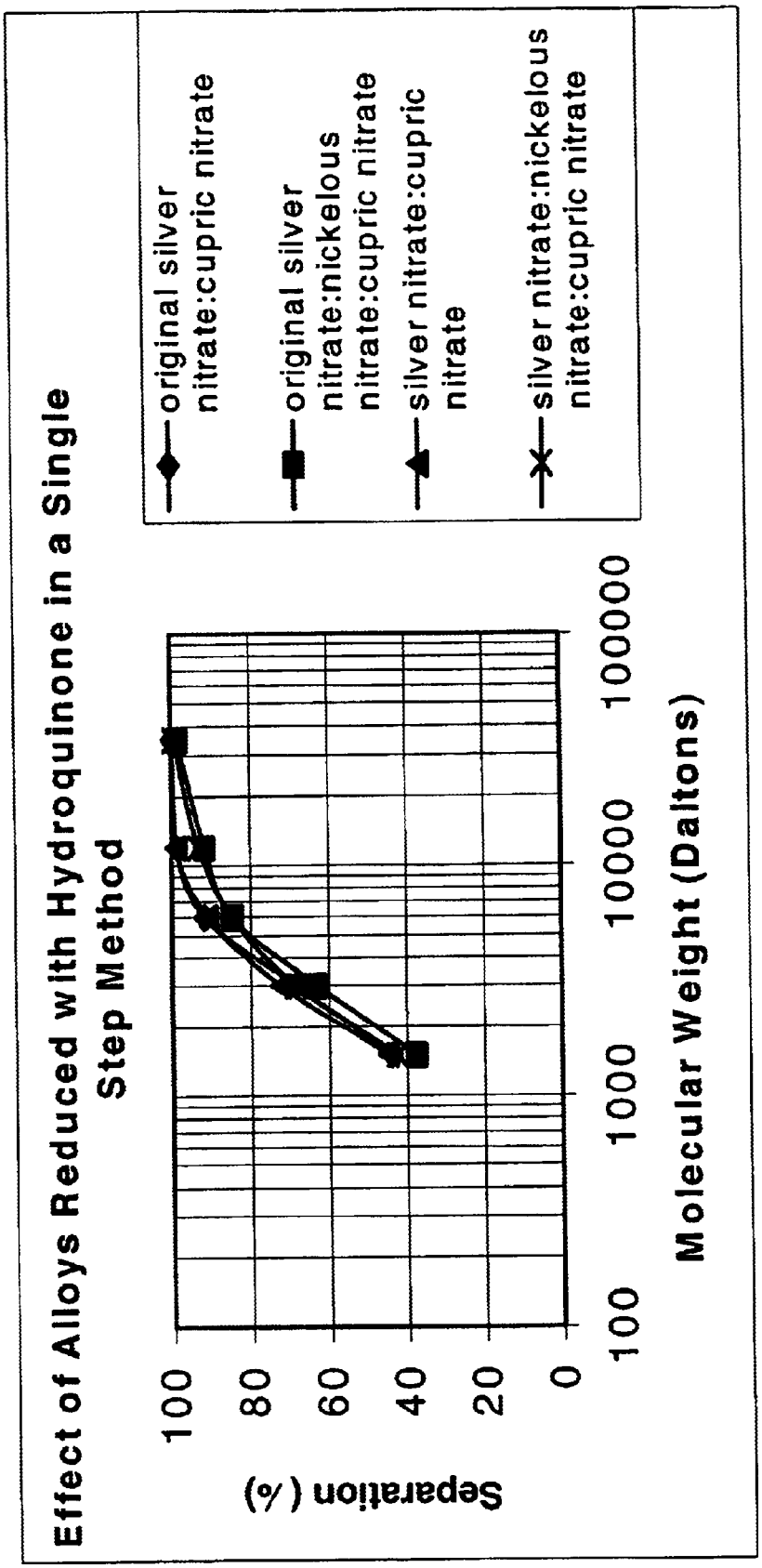
FIG. 4 is a graph illustrating the effect of the addition of metal alloys to the membrane, and reduced in situ by the single step method.

FIG. 4 shows the effect of the alloys in and on the active surface layer of the treated membranes. It is shown that the treated membranes gave PEG separation performance very similar to the original, untreated membranes. This indicates that although the metals are being deposited, as determined by the colour changes and negative *E. coli* testing, the membranes have retained their original porosity and minimal pore blockage has occurred.

The following were contacted in the listed sequence by draining the original solution, and added the next metal salt solution. Once completed, the membranes were reduced with 1% hydroquinone:

1. 6% nickelous nitrate then 6% cupric nitrate
2. 6% nickelous nitrate then 6% silver nitrate
3. 6% cupric nitrate then 6% silver nitrate
4. 6% cupric nitrate then 6% nickelous nitrate
5. 6% nickelous nitrate then 6% cupric nitrate then 6% silver nitrate

TABLE 10

Flux and Separation Data for Membranes with Alloys Reduced in the Single Step Method

| 25% PES-PEES - 21% PVP Reduced into 1% hydroquinone: | Before Treatment | | | After Treatment | | | change in PWP |
|---|---|---|---|---|---|---|---|
| | PWP (LMH) | 200 ppm PEG 6K (LMH) | % sep | PWP (LMH) | 200 ppm PEG 6K (LMH) | % sep | |
| 6% nickelous nitrate then 6% cupric nitrate | 165 | 148 | 89% | 129 | 111 | 88% | 0.778 |
| 6% nickelous nitrate then 6% silver nitrate | 175 | 165 | 91% | 131 | 118 | 85% | 0.749 |
| 6% cupric nitrate then 6% silver nitrate | 180 | 165 | 92% | 133 | 122 | 91% | 0.738 |
| 6% cupric nitrate then 6% nickelous nitrate | 189 | 172 | 85% | 138 | 124 | 90% | 0.730 |
| 6% nickelous nitrate then 6% cupric nitrate then 6% silver nitrate | 190 | 136 | 85% | 139 | 125 | 85% | 0.732 |

All the membranes were dark in colour except for the nickelous nitrate with cupric nitrate which only had a slight grey colour change. The membranes containing the three metal salts together resulted in a shiny metallic surface.

Method 2—Alloys Reduced in the Multi-Step Method

A 25% polyethersulfone-polyetherethersulfone co-polymer and 21% polyvinylpyrrolidinone in 1-methyl-2-pyrrolidinone on polyester backing membranes gelled into reverse osmosis water and treated with:

1. 100 ppm tin sulfate then 1% silver nitrate and 1% cupric sulfate
2. 100 ppm tin sulfate then 50 ppm palladium nitrate/50 ppm tin sulfate then 1% silver nitrate, 1% cupric sulfate and 1% nickelous nitrate
3. 100 ppm palladium nitrate for then 50 ppm palladium nitrate/50 ppm tin sulfate for then 1% silver nitrate, 1% cupric sulfate and 1% nickelous nitrate
4. 100 ppm palladium nitrate for then 1% nickelous nitrate The membrane contacted with 100 ppm tin sulfate then 1% silver nitrate and 1% cupric sulfate gave flux rates of 222 LMH with pure water and 221 LMH (76% separation) with PEG 6K. The membrane contacted with 100 ppm palladium nitrate then 1% nickelous nitrate gave pure water flux rates of 159 LMH and 157 LMH (82% separation) with PEG 6K. The tin sulfate and palladium nitrate were added as accelerators or initiators for the reduction of copper and nickel.

The following were contacted in the sequence listed. After each addition of metal salt, the metal on the membrane was reduced with 1% hydroquinone before the addition of the next metal salt.

1. 6% cupric nitrate then 6% silver nitrate
2. 6% nickelous nitrate then 6% cupric nitrate then 6% silver nitrate
3. 6% silver nitrate then 6% cupric nitrate
4. 6% silver nitrate then 6% cupric nitrate then 6% nickelous nitrate found during longer term permeation tests that when the membranes are reduced to the metal after each addition, the metals remain on the surface of the membrane for a longer time that if two or three metals are reduced all in one step.

Figure 5:
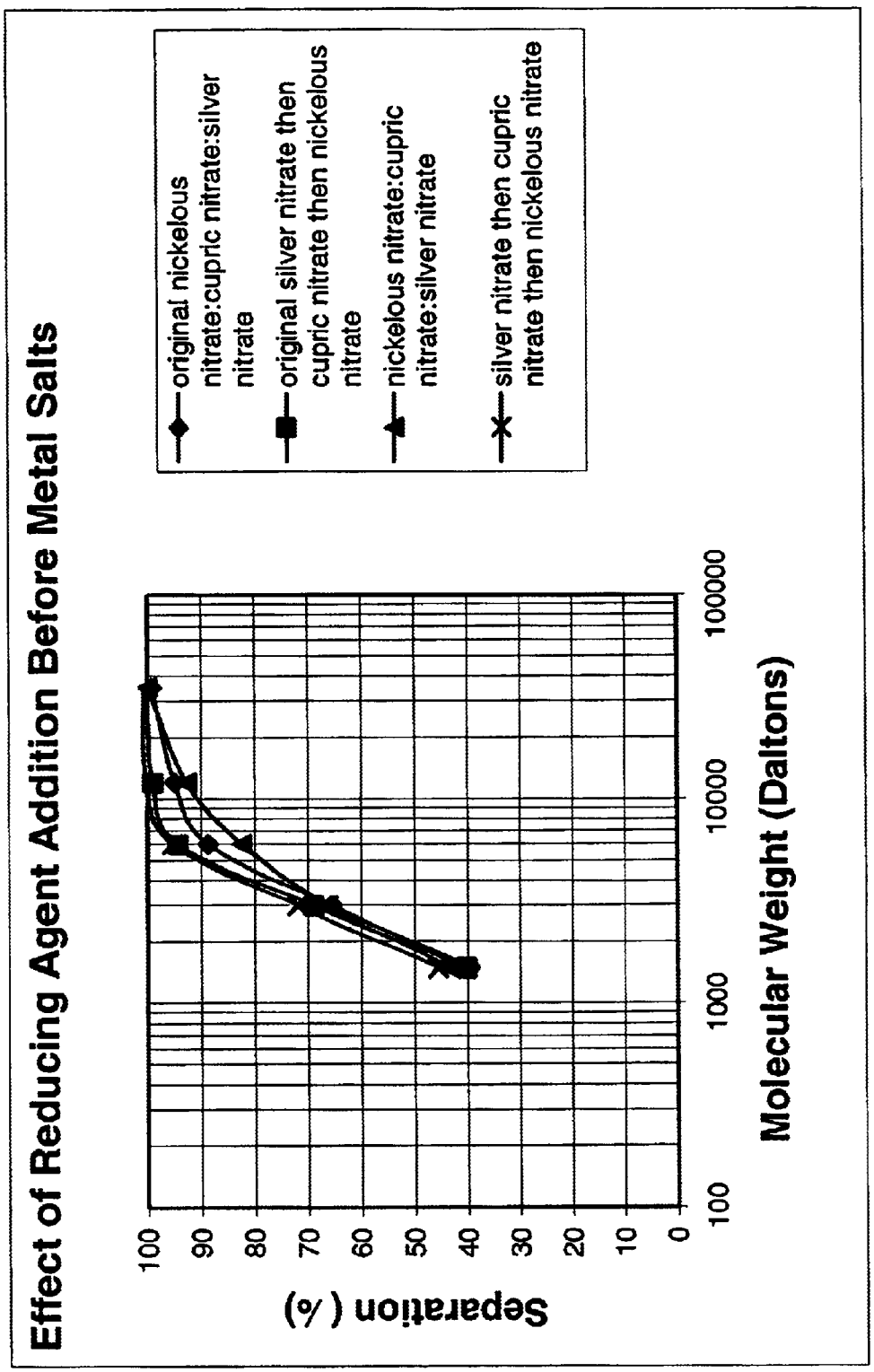
FIG. 5 is a graph illustrating the effect of the sequential addition of metals, by the multi-step method.

FIG. 5 shows the effect of the alloys reduced using the multi-step method on membrane performance. It is shown once again that the treated membranes gave PEG separation performance very similar to the original, untreated membranes.

Method 3—Alloys Reduced using Other Reducing Agents

A 25% polyethersulfone-polyetherethersulfone co-polymer (PES-PEES) and 21% polyvinylpyrrolidinone (PVP) in 1-methyl-2-pyrrolidinone solution cast onto polyester backing gelled into reverse osmosis water. These membranes were subjected to a silver nitrate deposit by the following method: To 38 mL of a 7% silver nitrate solution, ammonium hydroxide was added drop by drop until the dark brown precipitate dissolved. 13 mL of 14% potassium hydroxide was added and ammonium hydroxide added drop by drop until the solution became clear. 15 mL of a solution of 6.5% dextrose in 17.5% ethyl alcohol in distilled water was added. The solution was mixed for 1 minute and the membranes added and allowed to adsorb. This was followed by a static adsorption of 3.5% cupric sulfate, followed by a static adsorption of 3.5% zinc nitrate.

TABLE 11

Flux and Separation Data for Membranes with Alloys Reducing in the Multi-Step Method

| 25% PES-PEES - 21% PVP | Before Treatment | | | After Treatment | | | change in PWP |
|---|---|---|---|---|---|---|---|
| | PWP (LMH) | 200 ppm PEG 6K (LMH) | % sep | PWP (LMH) | 200 ppm PEG 6K (LMH) | % sep | |
| 6% cupric nitrate then 6% silver nitrate | 200 | 176 | 87% | 93 | 86 | 95% | 0.468 |
| 6% nickelous nitrate then 6% cupric nitrate then 6% silver nitrate | 196 | 173 | 84% | 99 | 85 | 89% | 0.507 |
| 6% silver nitrate then 6% cupric nitrate | 167 | 155 | 95% | 121 | 106 | 96% | 0.725 |
| 6% silver nitrate then 6% cupric nitrate then 6% nickelous nitrate | 162 | 117 | 92% | 117 | 100 | 91% | 0.719 |

All membranes were dark in colour. The membranes with silver nitrate as their last step had a metallic sheen. It was

TABLE 12

Flux and Separation Data for Membranes Reduced with Dextrose

| 25% PES-PEES - 21% PVP Silver deposited membranes | Before Treatment | | | After Treatment | | | change in |
|---|---|---|---|---|---|---|---|
| | PWP | 200 ppm PEG 6K | | PWP | 200 ppm PEG 6K | | |
| absorption of: | (LMH) | (LMH) | % sep | (LMH) | (LMH) | % sep | PWP |
| 3.5% cupric sulfate | 139 | 135 | 85% | 117 | 125 | 88% | 0.837 |
| 3.5% cupric sulfate then 3.5% zinc nitrate | 128 | 125 | 91% | 118 | 115 | 92% | 0.928 |
| Standard (no treatment) | 148 | 143 | 86% | | | | |

The membranes contacted with zinc nitrate were yellowish in colour. After testing, the colour remained on the surface.

Metal and Alloys Reduced on the Membrane using Reduction Step First

A 20% polyphenylsulfone, 20% polyvinylpyrrolidinone, 2% silver nitrate, and 2% hydroquinone in 1-methyl-2-pyrrolidinone solution was cast onto polyester backing and gelled into reverse osmosis water. This membrane gave a pure water flux rate of 609 LMH and PEG 35K flux rate of 463 LMH (27% separation). This has changed from the standard membrane of this type which gives pure water flux rates of 292 LMH and PEG 35K flux rates of 205 LMH (99% separation).

An 18% polyethersulfone-polyetherethersulfone co-polymer (PES-PEES), 18% polyvinylpyrrolidinone (PVP), and 5% hydroquinone in 1-methyl-2-pyrrolidinone solution was a cast onto polyolefin backing and gelled into 0.5% hydroquinone. Silver nitrate (6%) was sponged onto the surface of the membrane. By this method, as little or as much silver can be added. Cupric nitrate (6%) was also added in this method, but was slower to react. The concentration and the temperature of the solution was increased to shorten the time required for reaction.

TABLE 13

Flux and Separation Data for Membranes with Hydroquinone in the Casting Solution

| 18% PES-PEES - 18% PVP - 5% hydroquinone Gelled | PWP | 200 ppm PEG 6K | | 200 ppm PEG 35K | |
|---|---|---|---|---|---|
| into 0.5% hydroquinone | (LMH) | (LMH) | % sep | (LMH) | % sep |
| 6% silver nitrate sponged on surface | 659 | 624 | 16% | 405 | 72% |
| 6% cupric nitrate sponged on surface | 619 | 601 | 22% | 411 | 73% |
| Standard (no treatment) | 512 | 378 | 48% | 345 | 60% |

A 25% polyethersulfone-polyetherethersulfone co-polymer (PES-PEES) and 21% polyvinylpyrrolidinone (PVP) in 1-methyl-2-pyrrolidinone solution cast onto polyester backing and gelled into reverse osmosis water. These membranes were subjected to:

1. 1% hydroquinone then 6% total 1:1:1 nickelous nitrate:cupric nitrate:silver nitrate
2. A sequential treatment of 1% hydroquinone then 6% silver nitrate then 1% hydroquinone then 6% cupric nitrate then 1% hydroquinone then 6% nickelous nitrate

TABLE 14

Flux and Separation Data for Membranes Treated with Reducing Agent Before Metal Salts

| 25% PES-PEES - 21% PVP | Before Treatment | | | After Treatment | | | change in PWP |
|---|---|---|---|---|---|---|---|
| | PWP | 200 ppm PEG 6K | | PWP | 200 ppm PEG 6K | | |
| | (LMH) | (LMH) | % sep | (LMH) | (LMH) | % sep | |
| 1% hydroquinone then 6% total 1:1:1 nickelous nitrate:cupric nitrate:silver nitrate | 169 | 120 | 89% | 117 | 103 | 82% | 0.690 |
| 1% hydroquinone then 6% silver nitrate then 6% cupric nitrate then 6% nickelous nitrate | 132 | 124 | 94% | 94 | 82 | 95% | 0.711 |

The membranes were very dark in colour with a white surface and metallic sheen. By this method, the membranes retained their quality of metallic content better than those membranes contacted with the metal salt first.

Figure 6:
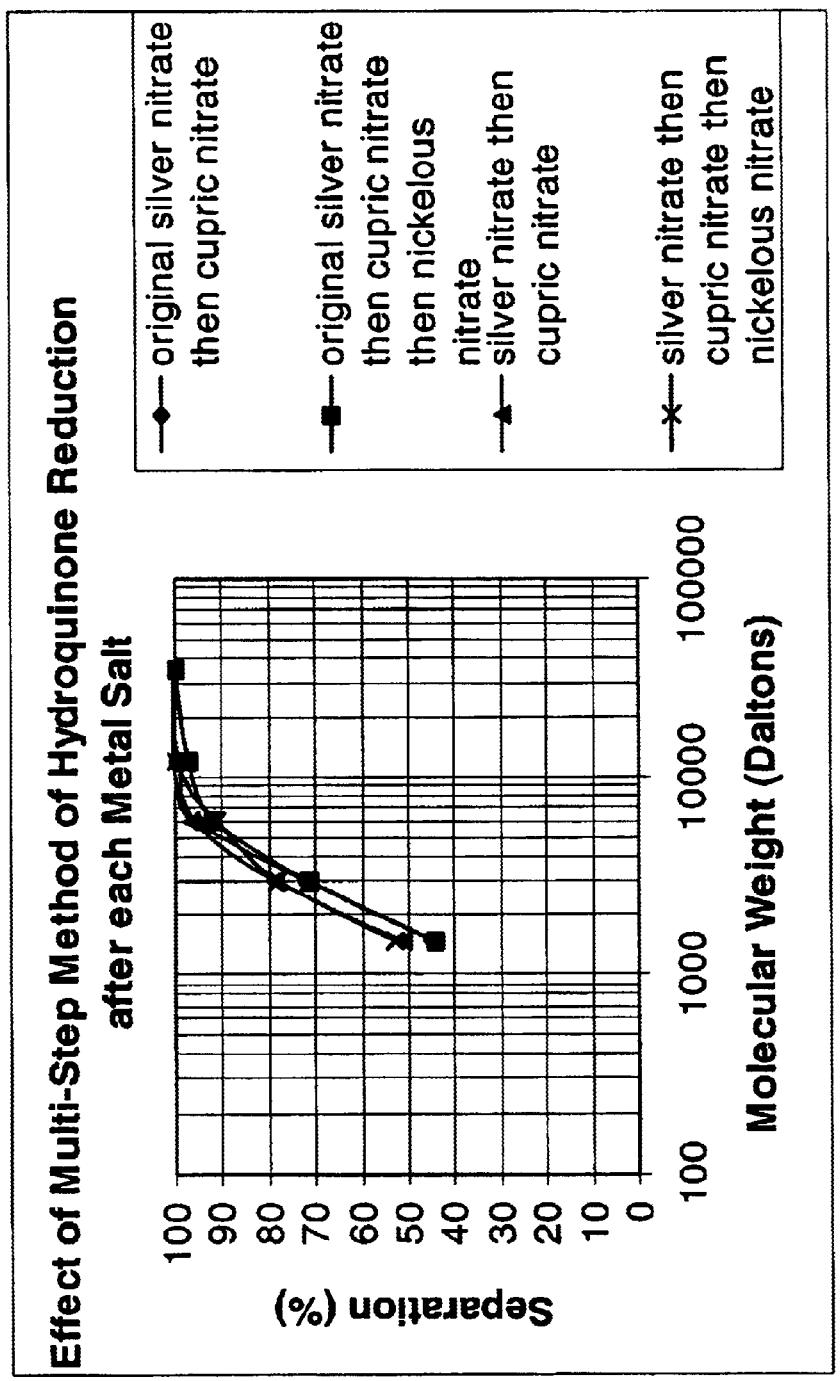
FIG. 6 is a graph illustrating the effect of the addition of the reducing agent before the metal alloys.

FIG. 6 shows the effects of the reducing agent addition before the metal salts. As shown, the treated membranes give a slightly lower molecular weight cut off value than the untreated membranes. This would be due to the incorporation of metals into the surface pores of the membrane. As discussed previously, a more open initial membrane could be chosen in order to obtain a tighter final, metal-treated membrane.

In the formation of hollow fibers, a casting solution was made with 25% polyethersulfone-polyetherethersulfone co-polymer (PES-PEES), 21% polyvinylpyrrolidinone (PVP), and 5% hydroquinone in 1-methyl-2-pyrrolidinone solution. The fiber was cast through a spinerette with 2% cupric nitrate, 2% nickelous nitrate and 2% silver nitrate solutions in the bore liquid to produce predominantly inside metalized fibers. With the same casting solution, but by using metal salts on the outside of the fiber, a predominantly outside metallization was obtained.

What is claimed is:

1. A process for making a bacteriostatic synthetic polymer membrane, comprising
    (a) providing a preformed porous synthetic polymer membrane, and
    (b) contacting the membrane with a bacteriostatic metal ion and a reducing agent for the metal ion which is non-toxic to animals, whereby the metal ion is attached to the polymer by static adsorption/absorption and is reduced to the metal in situ.

2. A process according to claim 1, for making a bacteriostatic synthetic polymer membrane, comprising the sequential steps of
    (a) providing a preformed porous synthetic polymer membrane,
    (b) contacting the membrane with a bacteriostatic metal ion, to attach the metal ion to the polymer by static adsorption/absorption, and
    (c) exposing the membrane to a reducing agent for the metal ion which is non-toxic to animals, to reduce the metal ion to the metal in situ.

3. A process according to claim 2, wherein steps (b) and (c) are sequentially repeated for successive additions of different bacteriostatic metal ions.

4. A process according to claim 1, for making a bacteriostatic synthetic polymer membrane, comprising the sequential steps of
    (a) providing a preformed porous synthetic polymer membrane,
    (b) contacting the membrane with a reducing agent for a bacteriostatic metal ion which is a non-toxic to animals, and
    (c) exposing the membrane to a bacteriostatic metal ion, whereby the metal ion is attached to the polymer by adsorption/absorption and is reduced to the metal in situ.

5. A process according to claim 4, wherein steps (b) and c) are sequentially repeated for successive additions of different bacteriostatic metal ions.

6. A process according to claim 1, for making a bacteriostatic synthetic polymer membrane, comprising simultaneously contacting a preformed porous synthetic polymer membrane with a solution containing a bacteriostatic metal ion and a reducing agent for the metal ion which is non-toxic to animals, whereby the metal ion is attached to the polymer by static adsorption/absorption and is reduced to the metal in situ.

7. A process for making a bacteriostatic synthetic polymer membrane, comprising
    (a) providing a synthetic membrane forming polymer, an organic solvent therefor and a bacteriostatic metal ion to form a membrane casting solution, and
    (b) gelling the casting solution into a bath containing a reducing agent for the metal ion which is non-toxic to animals, to reduce the metal ion to the metal in situ, to form the synthetic polymer membrane having the metal incorporated therein.

8. A process according to claim 1, wherein, the metal ion is in the form of an aqueous solution of a salt of the metal, comprising 0.25 to 15% w/w of the metal.

9. A process according to claim 8, wherein the reducing agent is included in an aqueous solution in an amount of 0.5 to 5% w/w of the reducing agent.

10. A process according to claim 9, wherein the metal is selected from the group consisting of silver, copper, nickel, tin and a mixture thereof.

11. A process according to claim 10, wherein the reducing agent is selected from the group consisting of hydroquinone, formaldehyde, reducing sugars and a mixture thereof.

12. A process according to claim 11, wherein the concentration of metal salt is 6% w/w, and in step c) the concentration of reducing agent is 1% w/w.

13. A process according to claim 12, wherein the polymer is selected from the group consisting of polyvinylalcohol, polyvinylidenefluoride, polysulfone, polyethersulfone-polyetherethersulfone copolymer, polyphenylsulfone, polyacrylonitrile, polyamide-imide copolymer and polyether-imide copolymer.

14. A process according to claim 13, wherein the metal ion is a mixture of silver and copper ions.

15. A process according to claim 7, wherein the metal ion is in the form of an aqueous solution of a salt of the metal, comprising 0.25 to 15% w/w of the metal.

16. A process according to claim 15, wherein the reducing agent is included in an aqueous solution in an amount of 0.5 to 5% w/w of the reducing agent.

17. A process according to claim 16, wherein the metal is selected from the group consisting of silver, copper, nickel, tin and a mixture thereof.

18. A process according to claim 17, wherein the reducing agent is selected from the group consisting of hydroquinone, formaldehyde and a mixture thereof.

19. A process according to claim 18, wherein the concentration of metal salt is 6% w/w and the concentration of reducing agent is 1% w/w.

20. A process according to claim 19, wherein the polymer is selected from the group consisting of polyvinylalcohol, polyvinylidenefluoride, polysulfone, polyethersulfone-polymetherethersulfone copolymer, polyphenylsulfone, polyacrylonitrile, polyamide-imide copolymer and polyether-imide copolymer.

21. A process according to claim 20, wherein the metal ion is a mixture of silver and copper ions.

22. A process for making a bacteriostatic membrane, comprising
   (a) providing a synthetic membrane forming polymer, an organic solvent therefor, a bacteriostatic metal ion and a reducing agent for the metal ion which is non-toxic to animals, to reduce the metal ion to the metal in situ, to form a membrane casting solution, and
   (b) gelling the casting solution into a water bath, to form the synthetic polymer membrane having the metal incorporated therein.

23. A composite synthetic polymer membrane, comprising a preformed synthetic polymer membrane and a bacteriostatic metal in free-form, attached to a surface of the membrane by static adsorption/absorption, wherein the surface is an active separation surface layer.

* * * * *